(12) United States Patent
Goldstein (10) Patent No.: US 8,372,343 B2
(45) Date of Patent: Feb. 12, 2013

(54) MULTIPLE COAGULATION TEST CARTRIDGE AND METHOD OF USING SAME

(76) Inventor: Sheldon Goldstein, New York, NY (US)

(*) Notice: Subject to any disclaimer, the term of this patent is extended or adjusted under 35 U.S.C. 154(b) by 1090 days.

(21) Appl. No.: 11/952,914

(22) Filed: Dec. 7, 2007

(65) Prior Publication Data

US 2009/0148882 A1    Jun. 11, 2009

(51) Int. Cl.
G01N 33/86 (2006.01)
G01N 33/00 (2006.01)
G01N 33/48 (2006.01)
A61J 1/06 (2006.01)
A61J 1/20 (2006.01)
C12Q 1/56 (2006.01)
C12M 1/34 (2006.01)
C12M 1/36 (2006.01)
C12M 1/18 (2006.01)

(52) U.S. Cl. .......... 422/73; 422/413; 422/552; 422/554; 435/13; 435/288.2; 435/288.4; 435/288.5; 435/267.6; 73/64.41

(58) Field of Classification Search .................. None
See application file for complete search history.

(56) References Cited

U.S. PATENT DOCUMENTS

| | | |
|---|---|---|
| 2,616,796 A | 11/1952 | Schilling |
| 3,302,452 A | 2/1967 | Leslie |
| 3,695,482 A | 10/1972 | Smith |
| 3,836,333 A | 9/1974 | Mintz |
| 3,918,908 A | 11/1975 | Moyer et al. |
| 4,000,972 A | 1/1977 | Braun et al. |
| 4,074,971 A | 2/1978 | Braun et al. |
| 4,105,411 A | 8/1978 | Biver |
| 4,125,327 A | 11/1978 | Margolis |
| 4,135,819 A | 1/1979 | Schmid-Schonbein |
| 4,443,408 A | 4/1984 | Mintz |
| 4,497,774 A | 2/1985 | Scordato |
| 4,534,939 A * | 8/1985 | Smith et al. ............... 422/430 |
| 4,640,896 A | 2/1987 | Farrell et al. |
| 4,659,550 A | 4/1987 | Schildknecht |
| 4,663,127 A | 5/1987 | Jackson et al. |
| 4,671,939 A | 6/1987 | Mintz |
| 4,752,449 A | 6/1988 | Jackson et al. |
| 4,782,026 A | 11/1988 | Baugh et al. |
| 4,865,984 A | 9/1989 | Nemerson et al. |
| 4,871,677 A | 10/1989 | Baugh et al. |

(Continued)

FOREIGN PATENT DOCUMENTS

| | | |
|---|---|---|
| DE | 3540661 | 5/1987 |
| WO | WO8910788 | 11/1989 |

(Continued)

*Primary Examiner* — Christine Foster
(74) *Attorney, Agent, or Firm* — Stroock & Stroock & Lavan LLP (57) ABSTRACT

Embodiments of the present invention relate to multiple coagulation test cartridges and methods of using such cartridges. In one embodiment the cartridge is a disposable single-use cartridge for use in evaluating blood clotting. The cartridge includes multiple containers, such as tubes, each of which includes one or more coagulation affecting substances. The containers can be pre-filled with substances in amounts suitable for use with a single patient's blood sample. The cartridge may include one or more containers, each of which has multiple sections, or volumes, each section storing a different coagulation affecting substance. In another embodiment the cartridge is used in a method for determining at least one appropriate coagulation affecting substance for modifying a patient's coagulation status using a multiple coagulation test system.

14 Claims, 6 Drawing Sheets

U.S. PATENT DOCUMENTS

| | | |
|---|---|---|
| 4,946,775 A | 8/1990 | Yin |
| 5,039,615 A * | 8/1991 | Takahata ........................ 436/44 |
| 5,302,348 A | 4/1994 | Cusack et al. |
| 5,366,869 A * | 11/1994 | Goldstein ....................... 435/13 |
| 5,951,951 A | 9/1999 | Lane et al. |
| 6,114,135 A * | 9/2000 | Goldstein ....................... 435/13 |
| 6,413,784 B1 * | 7/2002 | Lundsgaard et al. ......... 436/518 |
| 6,861,954 B2 | 3/2005 | Levin |
| 2003/0072676 A1 | 4/2003 | Fletcher-Haynes et al. |
| 2006/0147992 A1 | 7/2006 | Smith et al. |

FOREIGN PATENT DOCUMENTS

| | | |
|---|---|---|
| WO | WO9101383 | 2/1991 |
| WO | WO9116453 | 10/1991 |
| WO | WO0182793 | 11/2001 |
| WO | WO03083489 | 10/2003 |
| WO | WO2006/020773 A2 * | 2/2006 |

* cited by examiner

MULTIPLE COAGULATION TEST CARTRIDGE AND METHOD OF USING SAME

BACKGROUND OF THE INVENTION

1. Field of the Invention

This invention relates generally to systems and methods that facilitate medical diagnosis and treatment of patients with compromised coagulation function that results in bleeding or, conversely, overactive coagulation that results in abnormal blood clotting or thrombosis.

2. Description of Related Art

It is well known in the art to inhibit the coagulation of a patient's blood by administering various anticoagulant substances, such as, for example, heparin, to the blood, which compromises the patient's blood coagulation function (i.e., causes iatrogenic coagulopathy). Inhibiting the coagulation of blood in a patient is particularly useful during medical procedures which may, for example, utilize extracorporeal circulation, such as medical procedures including cardiopulmonary bypass for cardiovascular surgery, extracorporeal membrane oxygenation (ECMO), cardiac assist devices such as artificial hearts or intra-aortic balloon pumps, and hemodialysis. After the medical procedure requiring compromised coagulation function is completed, it is then often desirable to restore coagulation function in the blood of the patient. Again, it is well known in the art to restore coagulation function in the blood of a patient having compromised coagulation function by administering known agents, such as, for example, protamine or heparinase, that counteract the anticoagulant substance.

Systems and methods for testing the impact or effectiveness of anticoagulant and/or coagulant reagents are known. These systems perform tests that individually are generally very narrow, testing only one aspect of coagulation, and requiring very few reagents to be mixed with a patient's blood. These systems further require an operator to place bottles of reagents into automated analyzers (which then pipette reagents from the bottles into the patient blood or plasma samples) or to manually add reagents to the patient sample, as for example when an operator manually pipettes reagents into plasma, followed by manual placement in—a platelet aggregometer. Whether an automated pipette is used, or an operator manually uses a pipette, to introduce the coagulation affecting reagents, such reagents are serially provided, one after another. Regardless whether each reagent is obtained from a large, multi-dose vial/bottle or from a tube pack, the operator is still required to manually manipulate the reagents and deliver the reagents to the system reservoirs individually. In addition, because reagents can be supplied in varying forms and temperatures, e.g., frozen, refrigerated, native and lyophilized (requiring re-hydration and mixing and/or warming), the time required for the operator to prepare the reagents and deliver them to the reservoirs may be significant.

Additionally, such known systems are designed for fast throughput, namely, providing one large bottle of reagent for many patients so that many tests can be done rapidly. Since reagents are expensive, and large bottles have a very short shelf life once opened, hospitals frequently choose not to perform coagulation testing, or choose only to perform certain tests on limited days (holding samples sent to the lab for several days to batch them together) to ensure a larger number of patient samples in need of testing, so as not to waste reagents. Furthermore, hematology devices are sometimes built with refrigerated platforms for holding the large bottles of reagents to help prevent spoilage.

Furthermore, whenever a human element is introduced into any system, a chance for human error follows. The chance for error only increases as the number of tests, and the number of coagulation affecting reagents used per test, increases. With such systems and methods, there is a risk that an operator particularly under the stresses of an operating room environment, or the productivity requirements of a central laboratory, may not fill the reservoirs with the correct type, concentration or amount of reagent, and may thereby jeopardize the test results.

Thus, a need exists for an improved method and system for testing coagulation and/or anticoagulation substances and, more specifically, of delivering multiple such substances for testing with a patient's blood.

SUMMARY OF THE EMBODIMENTS OF THE INVENTION

Embodiments of the present invention satisfy the foregoing needs. One embodiment is a disposable single use cartridge for use in evaluating blood clotting. The cartridge includes multiple containers, each of which includes one or more coagulation affecting substances. The amounts of these substances are included in amounts suitable for use on a single patient blood sample. In certain embodiments, one or more of the containers comprising the cartridge includes multiple volumes, each containing a different substance.

Another embodiment is a method for determining at least one appropriate coagulation affecting substance for modifying a patient's coagulation status using a multiple coagulation test system having multiple test wells and multiple ports in fluid communication with the test wells. The method comprising providing a cartridge, which has multiple sealed containers that are pre-filled with different coagulation affecting substances in amounts suitable for use with a single patient. An amount of the patient's blood is introduced into each of the test wells, and the cartridge is coupled with the ports, the coupling of the cartridge with the ports causing the sealed containers to become unsealed and be placed in fluid communication with the ports. The coagulation affecting substances are introduced into the test wells and coagulation in the test wells is compared to determine at least one appropriate coagulation affecting substance for treating the patient. The used cartridge is removed and discarded.

DETAILED DESCRIPTION OF CERTAIN EMBODIMENTS

Certain embodiments of the present invention will be discussed with reference to the aforementioned figures, wherein like referenced numerals refer to like components. It should be noted that references in the specification to phrases such as "one embodiment" or "an embodiment" means that a particular feature, structure or characteristic described in connection with the embodiment is included in at least one embodiment of the invention but is not necessarily required to practice the invention, which shall be defined by the claims appended hereto. The appearances of phrases such as "in one embodiment" in various places in the specification are not necessarily, but can be, referring to same embodiment.

Figure 1:
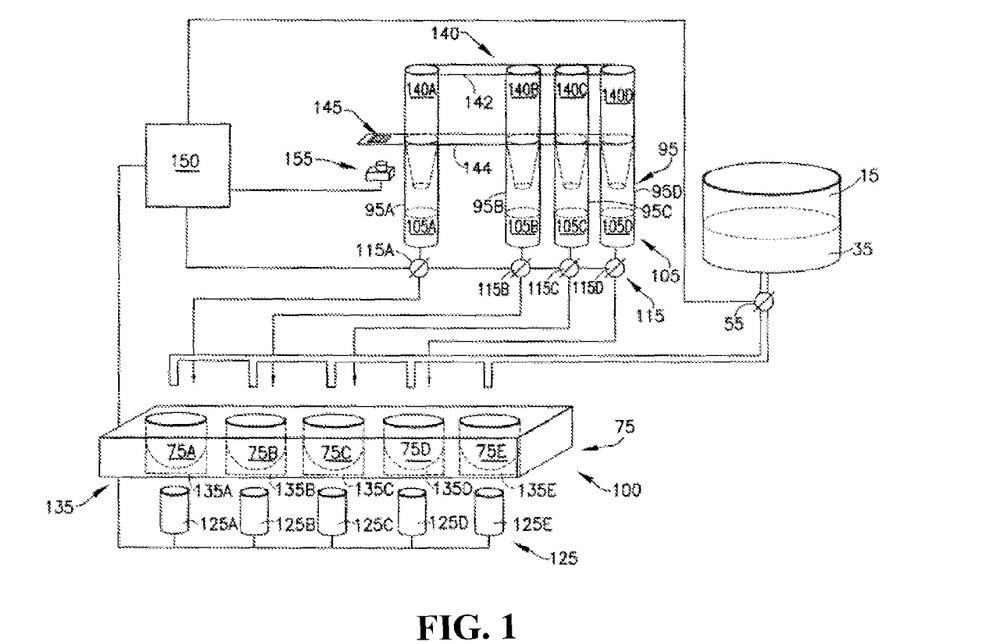
FIG. 1 is a schematic view showing one embodiment of a multiple coagulation test system (MCTS) utilizing a multiple coagulation test cartridge.

With reference to FIG. 1, a multiple coagulation test cartridge 140 according to one embodiment of the invention is shown in use with a multiple coagulation system (MCTS) 100, similar to the type shown and described in U.S. Pat. No. 6,114,135, entitled MULTIPLE COAGULATION TEST SYSTEM AND METHOD OF USING A MULTIPLE COAGULATION TEST SYSTEM, issued Sep. 5, 2000, hereby incorporated herein by reference. As described in greater detail in this patent, MCTS 100 may be used for determining an appropriate coagulation promoting or inhibiting substance for administration to a patient as a therapy for improving or inhibiting clotting function in the patient.

In general, the MCTS 100 includes a holder 15 for containing a patient's blood 35. An aliquot meter 55 is in fluid communication with the holder 15 for withdrawing predetermined measured amounts of the patient's blood 35. Each of various reservoirs 95A-D is to contain different coagulation promoting substances 105A-D. Each coagulation promoting substance 105A-D may be an agent or a combination of agents capable of improving clotting function or inhibiting clotting function in the patient depending on the application. Accordingly, it should be understood that reference to coagulation or anticoagulation substances (and similar terms) are non-limiting, and that use of both types of substances are within the scope of the present invention. Dosing meters 115A-D are in fluid communication with the reservoirs 95A-D for withdrawing preselected equivalent dose amounts of the coagulation promoting substances from the reservoirs 95A-D.

In one embodiment, MCTS 100 also contains wells 75A-D corresponding to each reservoir 95A-D and at least one additional well 75E for containing untreated blood 35 as a baseline or a standard which may function as a control. Each of the wells 75A-E receives a metered sample of blood 35 from holder 15 by being apportioned through aliquot meter 55. Well 75A receives a metered dose of coagulation promoting substance 105A through dosing meter 115A, well 75B receives a metered dose of coagulation promoting substance 105B through dosing meter 115B, and each additional well 75 corresponding to a reservoir 95 receives a metered dose of coagulation promoting substance 105 through dosing meter 115 as appropriate for the number of wells 75, reservoirs 95, and dosing meters 115. At least one additional well 75E contains blood 35 from holder 15 with no coagulation promoting substance 105 added. This additional well 75E is used to determine a baseline or standard coagulation time to function as a control. An appropriate therapy for improving clotting function in the patient is determined by comparison of the baseline clotting indicator time of the control sample with the clotting indicator times of the patient's blood 35 mixed with the coagulation promoting substances 105A-D.

MCTS 100 also includes coagulation detectors 125 (125A-E). Coagulation detectors 125A-E may be a photo-optical system or a magnetic system or other systems to evaluate clot formation or other clotting indicator. It should be noted that measurement of clot formation may be performed in any number of ways including, but not limited to, using devices such as an image detector, photo-optical detector, magnetic detector, etc, and measuring properties including, but not limited to, factor level, clot initiation, clot propagation, clot strength, viscosity, turbidometry, electrical impedance, etc, as long as the clotting results in the wells 75A-D can be compared to one another so as to achieve a medically relevant result. Additionally, the clot formation evaluating detector may be different for different coagulation promoting substances, i.e., a different clotting indicator may be used to assess the addition of platelets as compared to the clotting indicator for evaluating the addition of plasma. In order to test whether hypothermia is responsible for a patient's compromised coagulation function, MCTS 100 may further include temperature controllers 135 (135A-E for each well 75A-E).

MCTS 100 of the present embodiment has been configured to interface with cartridge 140 for use in filling the reservoirs 95A-D. It should be understood, however, that the cartridge 140 need not be the exclusive source of coagulation affecting substances for the MCTS 100. In alternate embodiments, for example, traditional pipette mechanism (automated and manual) may also be used. The cartridge 140 is preferably a pre-filled, single use per patient cartridge that is disposable, after use. Cartridge 140 preferably has a plurality of sealed, pre-filled containers, for example, four containers 140A-D. It should be noted that although four containers 140A-D are shown, cartridge 140 may include any number of containers. The containers 140A-D are preferably coupled together as a single cartridge 140, and the coupling may be accomplished by, for example, one or more connective structures 142, 144.

Each container 140A-D preferably contains a different individual or combination of coagulation promoting or inhibiting substances for use in the MCTS 100. Containers 140A-D may also contain any type of reagent or substance (or combination) that affects coagulation function. In various embodiments the coagulation affecting substances may be thought of as coming from three categories: 1) activators or inhibitors of coagulation, 2) blood products, and 3) pharmaceuticals. The category of activators or inhibitors of coagulation includes, but is not limited to, (alone or in combination) tissue factor, tissue thromboplastin, brain thromboplastin, diatomaceous earth, kaolin, calcium chloride, calcium gluconate, protamine, heparinase, phospholipids, brain phospholipids, ADP, collagen, glass beads, celite, kaolin, serotonin, fibrinogen coated glass beads, fibrinogen coated albumin microcapsules, protein coated albumin microspheres, epinephrine, ristocetin, arachadonic acid, thrombin, Thrombin Receptor Agonist Peptide (TRAP), heparin or sodium citrate.

The category of blood products includes, but is not limited to, human, bovine, porcine, recombinant, and lyophilized blood cells and/or proteins including, for example: platelets, cryoprecipitate, plasma, factors I (fibrinogen), II (prothrombin), III (tissue thromboplastin or tissue factor), IV (ionized calcium), V (labile factor or proaccelerin), Factor VII (stable factor or proconvertin), Factor VIII (anti-hemophilic factor), Factor IX (plasma thromboplastin component or Christmas factor), Factor X (Stuart-Prower factor), Factor XI (plasma thromboplastin antecedent), Factor XII (Hageman factor), Factor XIII (fibrin-stabilizing factor), von Willebrand Factor and fibronection. It is envisioned that therapeutically active freeze-dried platelets will be of particular suitability for use with cartridges of the present invention. Although not currently used in traditional coagulation tests, such are believed effective and, like other, coagulation affecting substances can be stored in a refrigerated state, thus included together in a single cartridge. These therapeutically active freeze-dried platelets are to be distinguished from those currently used as part of a ristocetin cofactor platelet reagent, because a ristocetin cofactor platelet reagent manifests only glyocoprotein Ib receptor activity, while the freeze-dried therapeutically active platelets having particular suitability for use with the single use cartridges within the scope of the present invention will also manifest glycoprotein IIb/IIIa expression and secretory function, the amount of glycoprotein IIb/IIIa expression and secretory function varying with manufacturing processes of said therapeutically active freeze dried platelets. It should be appreciated that using a blood product in the cartridge (in conjunction with multiple other substances) and in multiple tests facilitates determination of an optimal therapy a patient should receive to modify the patient's coagulation system in a beneficial manner.

The category of coagulation-affecting pharmaceuticals includes, but is not limited to, (alone or combination) epsilon amino caproic acid, tranexamic acid, desmopressin acetate, aprotinin, fibrinogen-coated albumin microcapsules, protein-coated albumin microspheres, and recombinant coagulation factors such as recombinant VIa, or sterilized/pasteurized coagulation factors, such as Factor VIII (antihemophilic factor) anti-inhibitor coagulant, von Willebrand Factor, Factor XI, Factor IX, Factor XIII and fibrinogen. It should be appreciated that the preceding list of coagulation-affecting substances is not exclusive, and other substances may be used so long as they affect coagulation. It should be further noted that substances from each category of such substances may be used in combinations with substances from the same category, or one or more other categories, and that combinations of any number of substances are possible.

The cartridge 140, by virtue of being pre-filled has several advantages. For example, cartridge 140 eliminates the need of the need to manually fill reservoirs 95A-D, as one cartridge 140 is used to fill all of the reservoirs 95A-D. Coagulation promoting or inhibiting substances typically come in large, multi-dose containers and have a limited shelf life once they have been opened and exposed to room temperatures. As a result, large amounts of coagulation promoting or inhibiting substances end up being discarded due to not being used within the allowed time after opening. Additionally, the use of cartridge 140 removes the need to fill each reservoir 95A-D individually, thereby expediting the filling process (by having all the reservoirs 95A-D filled simultaneously) and removing the chance of an operator improperly filling reservoirs 95A-D (e.g., either by using the wrong substance, the wrong concentration of a substance or the wrong amount of a substance).

In use, the cartridge 140 is inserted into or otherwise placed in fluid communication with the reservoirs 95A-D and the contents of the containers 140A-D are released into the reservoirs 95A-D. Subsequently, the coagulation testing may be performed by the MCTS 100.

Cartridge 140 may further include an identifier 145, which can be a physical, optical, electrical or other identification means, such as a radio frequency identification (RFID) tag, barcode, pin code or other identifier. Identifier 145 may contain any relevant information including, but not limited to, information related to the types, amounts, concentrations, and other properties of the substance, or substances, housed in each container 140A-D, or the entire cartridge 140.

The present embodiment further includes module 150, which may be a computer or other processor and associated memory operating according software, firmware or the like. Module 150 is coupled to reader 155, as well as aliquot meter 55 and dosing meters 115A-D. In general, reader 155 obtains information from the identifier 145 and transmits the information to module 150, which uses the information received from reader 155 and information stored in memory to provide control signals to the aliquot 55 and dosing meters 115A-D to deposit the appropriate amount of blood 35 and each coagulation substance 105A-D in each of the corresponding wells 75A-D. The information stored in memory used to control the aliquot 55 and dosing meters 115A-D may include, for example, a look-up table correlating the information received from the reader 155 identifying the cartridge 140 and/or particular substances 105A-D contained therein, with the appropriate controls to cause the appropriate amounts (and/or timing) of coagulation substance 105A-D to be deposited in each well 75A-D. Alternatively, the identifier 145 may directly provide instructions to the module 150 as to how much coagulation substance 105A-D and/or blood 35 should be deposited in the wells 75A-E. In certain embodiments it may be possible for several containers to be inserted, or in fluid communication with a single reservoir. Similarly, although FIG. 1 illustrates each reservoir 95A-D in fluid communication with a distinct well 75A-D, two or more reservoirs may be in fluid communication with a single testing well, thereby allowing for combinations of substances at the time of testing. In such an embodiment identifier 145 may provide the module 150 with information as to the amount of each substance to deposit (via control signals to the corresponding dosing meters 115A-D), the timing of such deposition of each substance and other relevant information. In further embodiments one container 140A-D and/or reservoir 95A-D may be in fluid communication with multiple wells 75A-D.

Generally speaking, as further described in U.S. Pat. No. 6,114,135, certain coagulation promoting substances need to be mixed with blood at different rates and proportions than other coagulation promoting substances. Accordingly, upon receiving information related to the proportions and/or types of coagulation promoting substances 105A-D contained within the containers 140A-D from the identifier 145, the module 150, preferably adjusts the respective dosing meters 115A-D to account for these factors, by, for example, opening a dosing meter to a greater/lesser degree or for a longer/shorter period than other dosing meter(s), or opening a dosing meter at a later/earlier time than other dosing meter(s), or opening dosing meter(s) for greater/fewer intermittent intervals than other dosing meter(s). It should be appreciated that the module 150 can customize the operation of the dosing meters in any medically relevant way.

In various embodiments it is possible for reader 155 to be a camera, an automated scanner, a human operated scanner, a receiving antenna, or any instrument capable of processing identification information.

It should be understood that although identifier 145 is illustrated as a single identifier, multiple identifiers may be used, for example, one identifier corresponding to each container 140A-D. Accordingly, a corresponding, or any number of readers may be used.

Furthermore, it should be understood that it is within the scope of the present invention to include embodiments without an identifier and reader. In such embodiments, the system can be manually controlled, pre-programmed or controlled via other means.

The cartridge 140 may be configured to ensure proper insertion into the reservoirs 95. For example, as shown in FIG.

1, the containers 105A-D may be asymmetrically coupled together, or such that the spacing among containers 140A-D is not uniform, thereby allowing insertion of the cartridge 140 in only one position. Other asymmetrical arrangements or other structures for ensuring proper installation of the container 140A-D are possible, so long as the functionality is not jeopardized.

While cartridge 140 is shown having a linear arrangement, it is possible to arrange the containers 140A-D in any other symmetrical or asymmetrical arrangement including, but not limited to, circular, rectangular, polygonal, L-Shaped, two-dimensional arrangements (e.g., multiple rows and the like). For example, the MCTS may be configured to have the wells 75A-D in a circular formation (not shown), in which case the containers 140A-D of cartridge 140 would have a corresponding circular formation (not shown).

Figure 2:
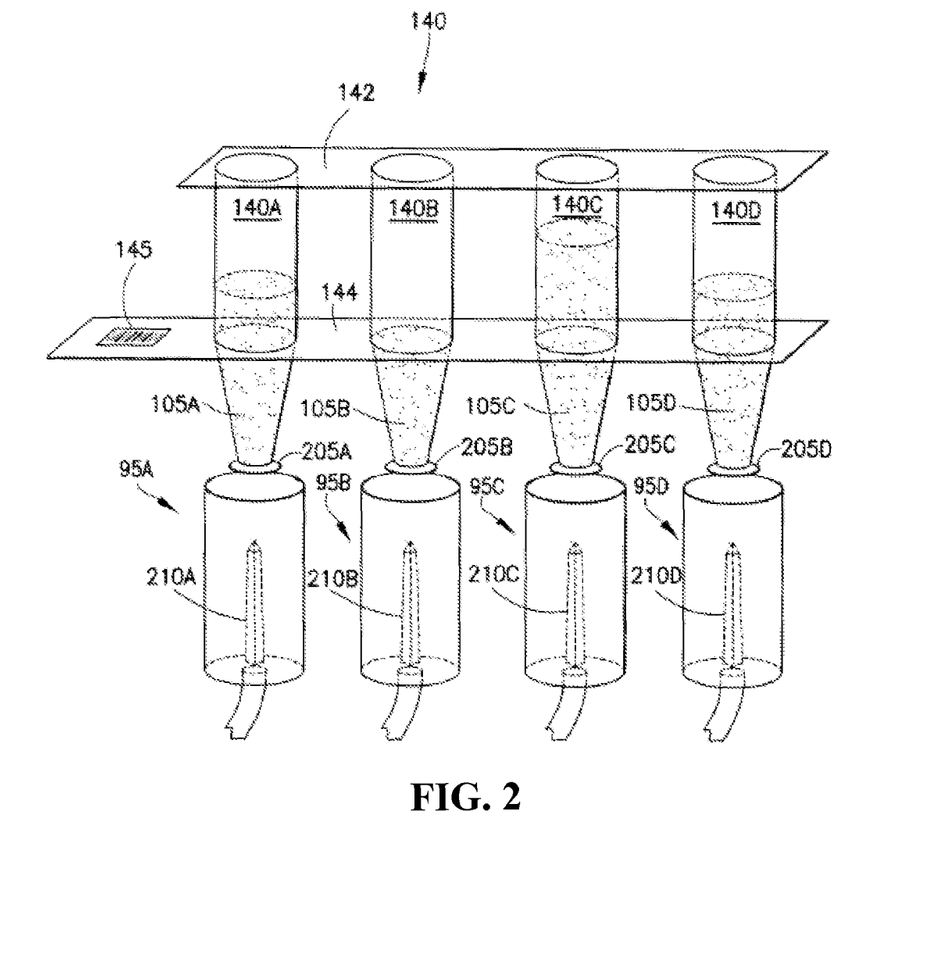
FIG. 2 is a perspective view of a multiple coagulation test cartridge system according to one embodiments of the present invention.

With reference to FIG. 2, a further described embodiment of a multiple coagulation test cartridge 140 in its pre-inserted state will now be described. Cartridge 140 may include four sealed cylindrical containers 140A-D with conical ends. As with other embodiments it should be appreciated that the containers may be any shape, such as cubical, spherical, etc. and the ends of each container may be any shape, for example, cylindrical, a beveled funnel, etc. As shown, each container 140A-D may be pre-filled with varying amounts of different individual or combination of coagulation promoting or inhibiting substances 105A-D. Each container 140A-D is preferably sealed, including at one end by membranes 205A-D.

Although sealed for safe and sanitary transport, containers 140A-D are configured to be opened so that the substances 105A-D may be deposited into reservoirs 95A-D. It will be apparent to those skilled in the art that containers 140A-D may be opened in any number of ways. For example, in the present embodiment, membranes 205A-D may be membranes of any composition that does not adversely affect the function of the system or the substances 105A-D, including, but not limited to, polypropylene, plastic, wax, polymer, foil, and other substances sealing to the end of each container 140A-D. The membranes 205A-D may, but do not have to, have the same shape or composition.

Membrane 205A-D are preferably configured to release the contents of cylinders 140A-D after, or as a result of insertion into reservoirs 95A-D. It is to be understood that the membranes described herein may be puncturable, removable, dissolvable or otherwise deformable to permit release of the substances when desired. For example, as shown in FIG. 2, the reservoirs 95A-D of MCTS 100 may be configured to include puncture elements 210A-D. Each puncture element 210A-D is preferably configured to penetrate the corresponding membrane 205A-D and permit the draining of the coagulation substances 105A-D into the reservoirs 95A-D. Each of puncture elements 210A-D may be an obelisk-shaped needle that may include grooves along its sides or an enlarged tip or may be hollow with various apertures to allow for faster draining of the substances 105A-D into the reservoirs 95A-D. As long as the puncture element 210A-D is capable of releasing substances 105A-D, the puncture element 210A-D may also be any other shape such as a blade, and any length. The puncture element 210C may also be a different type of mechanism such as, by way of a non-limiting example, a cutting implement that slices off membrane 205A-D (not shown) or a telescoping element whose height/length can be manually or automatically adjusted (including based on identifier 145). Additionally, the connective structure 142 may also be a membrane capable of being punctured, and the puncture elements 210A-D may be sized and configured to puncture it as well in order to facilitate the draining of the coagulation substances 105A-D. In some embodiments, the puncture element may be controlled by module 150 and a motor in accordance with information provided by the identifier 145, including, but not limited to, the rate or speed at which the puncturing element punctures containers 140A-D and/or membranes within each container 140A-D, the time at which the puncturing element punctures each container 140A-D, or membrane (e.g., by controlling the height of the puncture element vis a vis the membranes).

It should also be appreciated that various other methods of releasing the contents of containers 140A-D are possible, for example, the membrane 205 may be adhered to the cylinders 140A-D with a releasable adhesive, such that the membrane 205 may be peeled away prior to inserting the cartridge 140 into reservoirs 95. Alternatively, a puncture element could be used to puncture the membrane from the top (e.g., through structure 142), or within, each container 140A-D. Membranes 205 may be made in a variety of shapes and sizes; for example, it may also be a single structure that seals all of the containers 140A-D (not shown), in which case it is preferably made out of soft stretchable plastic, or brittle breakaway plastic that permits the insertion of the cylinders into the reservoirs.

It should be appreciated that reservoirs 95A-D serve as ports or receptacles for receiving the containers of the cartridge and an additional volume to store the substances need not be provided. For example, in alternate embodiments cartridge 140 may be placed in communication with testing wells 75A-D without the use of reservoirs 95A-D. In one such embodiment, for example, a plurality of ports that are in fluid communication with testing wells 75A-D may be used, and the containers 140A-D themselves serve as the reservoirs.

Figure 3:
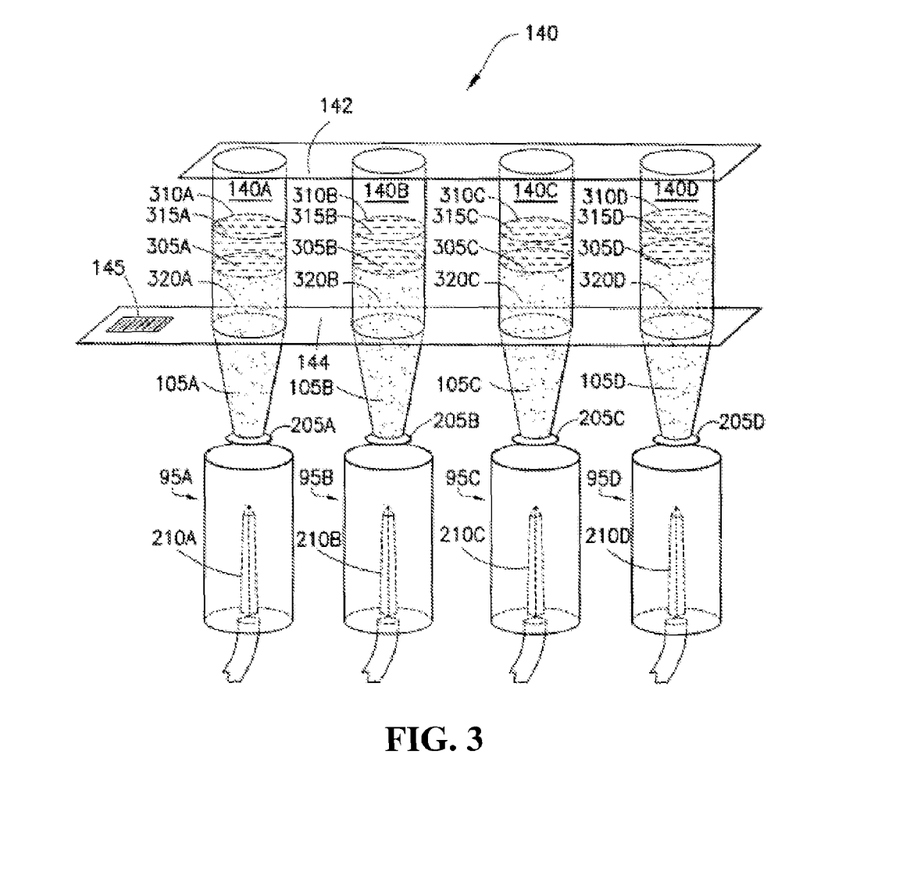
FIG. 3 is a perspective view of another embodiment of a multiple coagulation test cartridge system.

With reference to FIG. 3, an alternate embodiment of a multiple coagulation test cartridge 140 in its pre-inserted state will now be described. Each of the containers 140A-D may be pre-filled with a plurality of various amounts of different individual or combination of coagulation promoting or inhibiting substances, each separated from another by a membrane. For example, a container 140A may include membranes 305A and 310A, each setting off an appropriately sized section or volume of container 140A, with each section being pre-filled with a different coagulation substance 315A, 320A. It has been found that use of platelet reagents alone may not be sufficient for certain coagulation tests, and that activators (or inhibitors) and/or other reagents may need to be used. For example, such activators/inhibitors and/or reagents can be included in a container 140A-D that also contains platelets. It is foreseen that tests will utilize, for example, a combination of two to seven coagulation affecting substances, including activators, reagents, pharmaceuticals and/or blood products within each of one or more containers 140A-D.

In use, insertion of the cartridge 140 into the reservoirs 95A-D preferably results in the draining of the contents of containers 140A-D into the reservoirs 95A-D. This preferably occurs as a result of the piercing (at the same or different times) of all of the membranes 305A-D, 310A-D of a given container 140A-D, by the corresponding puncture element 210A-D or some other mechanism for emptying the contents into the corresponding reservoir 95A-D.

Figure 4A:
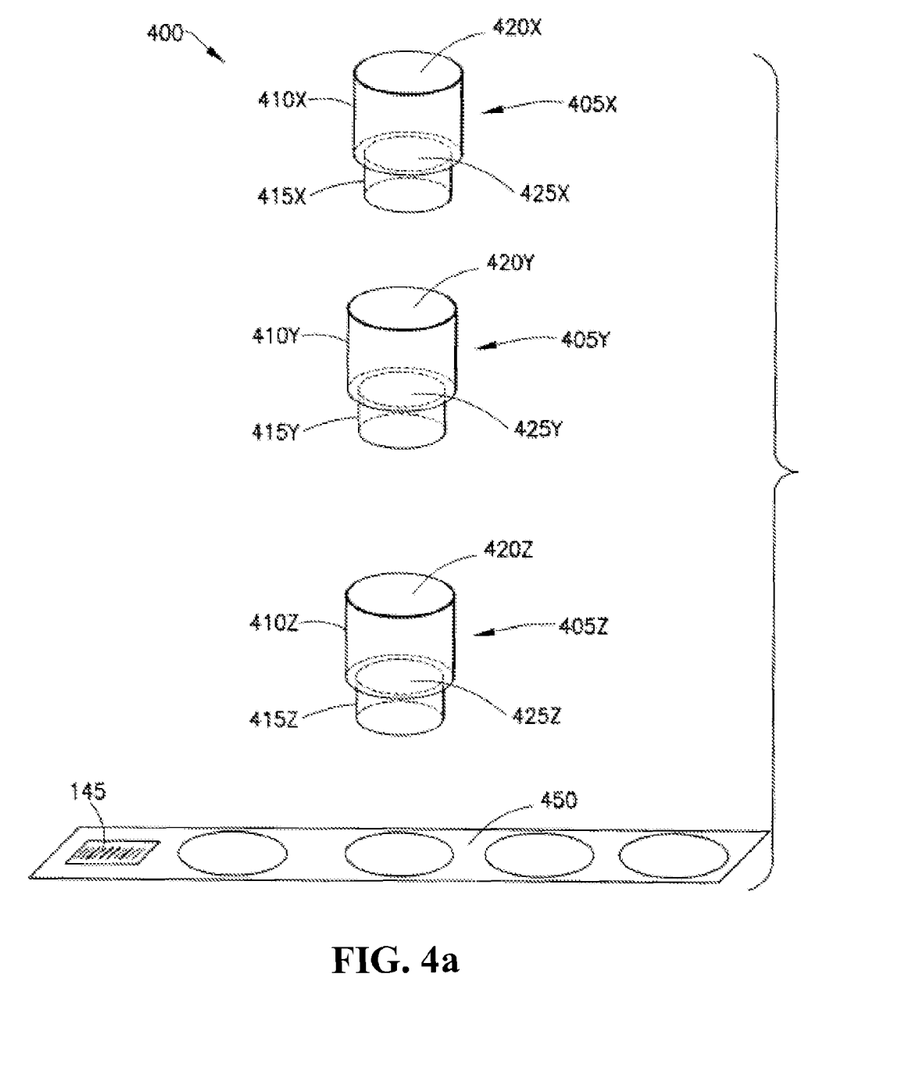
FIG. 4a is an exploded perspective view of a representative container of a multiple coagulation test cartridge according to one embodiment of the present invention.
Figure 4B:
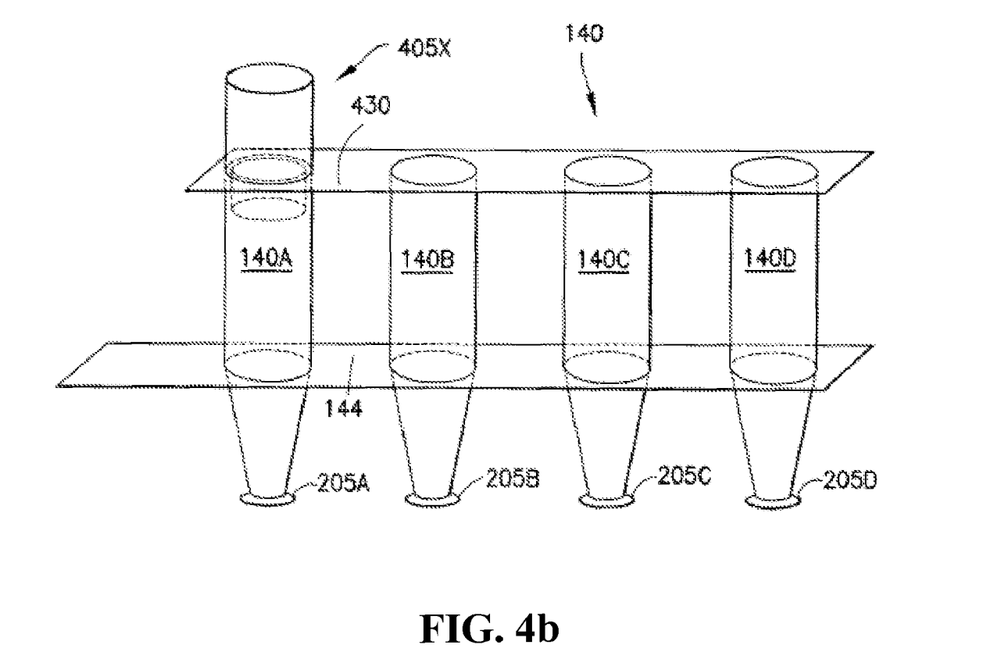
FIG. 4b is a perspective view of a multiple coagulation test cartridge according to one embodiment of the present invention.
Figure 5:
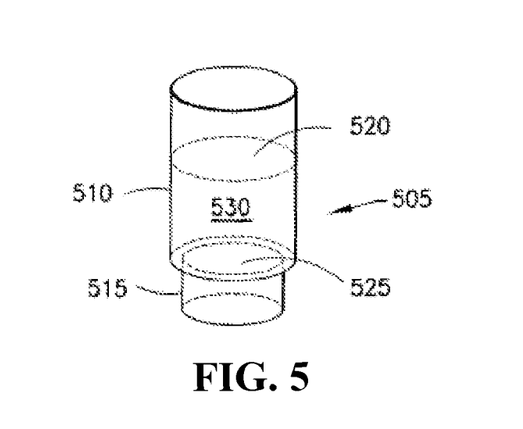
FIG. 5 is an exploded perspective view of a representative container of a multiple coagulation test cartridge according to one embodiment of the present invention.

With reference to FIGS. 4a, 4b, and 5, embodiments of customizable multiple coagulation test cartridges 140 will now be described. Generally speaking, a customizable container 400 of a multiple coagulation test cartridge may be made from a plurality of sections 405X-Z that, in use, may be assembled together by an operator of the cartridge 140 by, for example, snapping the sections 405X-Z into one another to form one or more containers of a cartridge. (Although only one container 400 is illustrated, a cartridge may include multiple such containers, which may be coupled together, for example, by a holder 450, into which the assembled containers are inserted.) Subsequent to the assembly, the cartridge 140 may be inserted into the reservoirs 95A-D, which preferably results in the unsealing of the plurality of sections (e.g., by a puncture element previously described), and the draining of the contents of sections 405X-Z into respective reservoirs 95A-D. Alternatively, the containers formed from the combination of sections 405X-Z may be inserted directly into a port, reservoir, or holder without otherwise being coupled to one another. It should be noted that any number of sections 405 may be used to form a container of a customizable multiple coagulation test cartridge.

As generally shown in FIG. 4a, in an embodiment of the customizable multiple coagulation test cartridge, each of the pre-filled sections 405X-Z preferably includes a main, top chamber 410X-Z having a given diameter and a second, bottom chamber 415X-Z, having a smaller diameter. The top chamber 410X-Z is sealed on one end by a membrane 420X-Z and sealed on the second end by a second membrane 425X-Z, thereby creating a volume for a coagulation/anticoagulation substance. Bottom chamber 415X of one section 405X is preferably sized and configured to be snugly inserted into the top chamber of 410Y of another section 405Y, thereby coupling the two sections 405X, 405Y together by, for example, tightly fitting inside the walls of the top chamber 410Y. Inserting a bottom chamber 405X into a top chamber 410Y may also rupture membrane 420Y of the second section 405Y.

As generally shown in FIG. 4b, where the top 430 of the containers is open (for example, after a seal is removed) or is a puncturable membrane, an operator may snap a section 405X into a container 140A of the cartridge 140, thereby creating a customized, multi-section container 140A. In use, the puncture element of the reservoir (not shown) is preferably long enough to pierce through all of the membranes of such customized, multi-section container 140A.

As generally shown in FIG. 5, pre-filled sections 505 of the customizable multiple coagulation test cartridge may be constructed generally as the sections of FIG. 4a but wherein the top chamber 510 is sealed along its length (as opposed to its end) by a first membrane 520, and at an end by a second membrane 525, wherein the walls of the chamber 510 extend beyond the membrane 520. Thus, a volume is defined by the membranes 520, 525 for containing the substance 530. As a result, the connection of one section 505 to another section, in the manner described above with reference to FIGS. 4a and 4b, will not result in the breaking of membrane 520, thus decreasing the risk of the spilling of the contents of chamber 510. A puncture element (as described above) may be used to pierce the membranes 520, 525 when inserted into a reservoir.

Although the connection of the various pre-filled sections of FIGS. 4a-b and 5 have been described as a mechanical coupling by fitting the sections together, it should be appreciated that any other method of coupling may be utilized, for example, the sections may be glued, threadably engaged, melted together, or otherwise secured. It should be further appreciated that the structure of pre-filled sections may be adjusted accordingly, in response to the method chosen for coupling. For example, if threadable engagement is chosen as a coupling mechanism, then the section 505 may be configured to have threads on the interior of the walls of the top chamber 510 that extend beyond the membrane 520, and mating threads on the exterior of the bottom chamber 515. Additionally, if the threaded coupling is being performed by the manufacturer, as opposed to the operator, costs of manufacturing may be lowered by utilizing only a single membrane 525, per section 505. In other embodiments each section includes only a bottom membrane (e.g., 525, 425X-Z such that the section may be filled with a substance and sealed by the membrane of another section when that other section is coupled to the top of it. The membranes of FIGS. 4a-b and 5 may take any suitable form, such as polypropylene, plastic, wax, polymer, foil and other materials.

Figure 6:
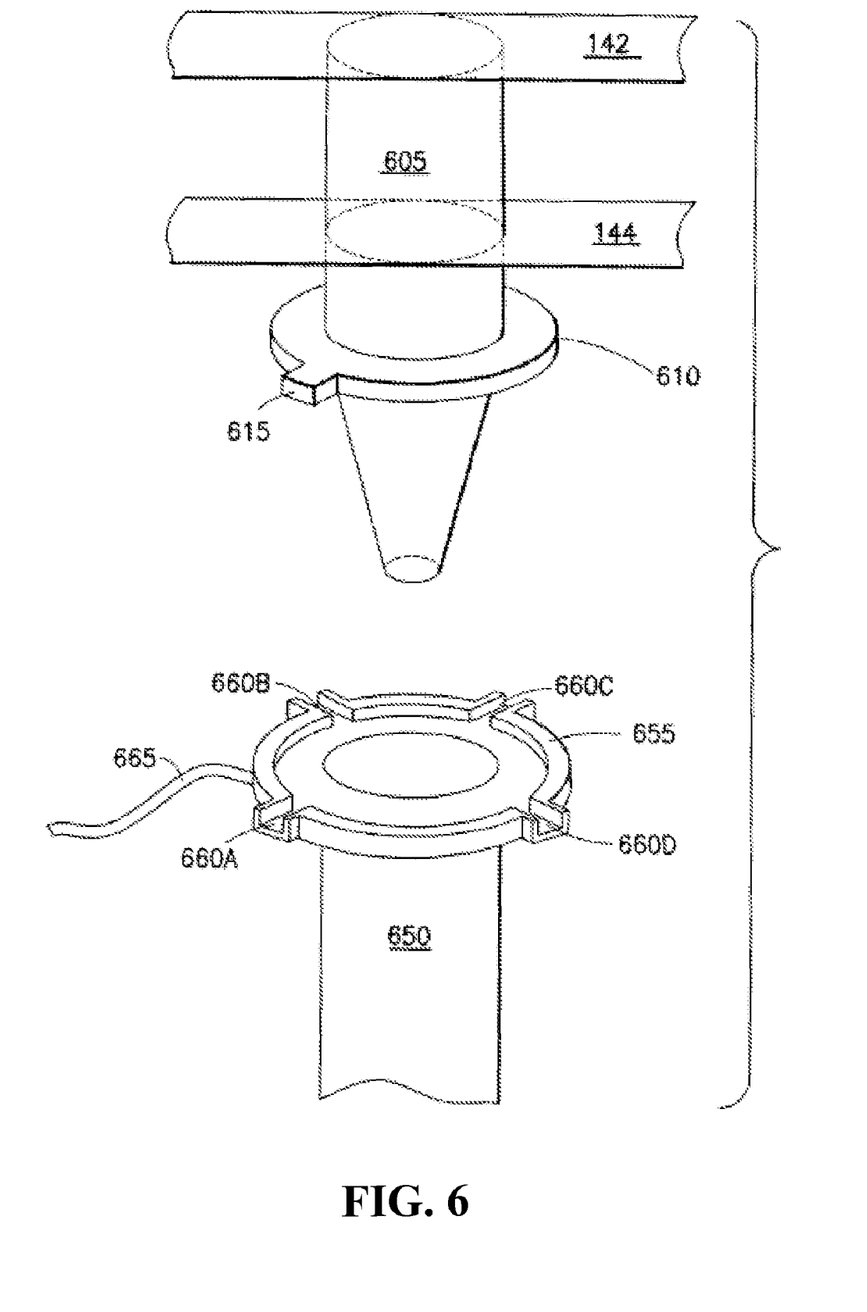
FIG. 6 is a perspective view of a representative container of a multiple coagulation test cartridge according to one embodiment of the present invention.

With reference to FIG. 6, an alternate embodiment of the multiple coagulation test cartridge will now be described. For ease of illustration and description, only a single container 605 of a cartridge is shown. In general, container 605 of the cartridge is configured to fit within a corresponding reservoir 650 in way that may be used by a module 150 (seen in FIG. 1) to determine the contents of the container 605 of the cartridge 140. For example, each container preferably includes, around its outside perimeter, a stopper member 610 which includes one or more protrusions or other indicators 615. The cartridges may be manufactured such that the arrangement of protrusions 615 may be used as an identifying characteristic of the substances within the container. For example, a single protrusion 615 may indicate heparin, while two protrusions 615, or a protrusion 615 in a different position, may indicate protamine. Each reservoir preferably includes a collar 655 with a plurality sensors 660A-D for receiving the member 610 and protrusions 615 of the container 605. In use, when the container 605 of the cartridge 140 is inserted into the reservoir 650, the stopper 610 preferably fits into collar 655, and the one or more protrusions 615 preferably fit into the plurality of recesses housing the sensors 660A-D, the specific position being detected by sensor 660A-D and transmitted to module 150, by coupling 665. The sensors 660A-D may take any number of forms, for example, an electric latch that is closed by protrusion 615. Thereafter, the module 150 preferably adjusts the working of automated testing system 100 accordingly by, for example, adjusting the aliquot meter 55 and dosing meters 115A-D.

In still other embodiments, the mixing of the contents of the cartridge containers may occur inside containers 140A-D prior to insertion. This may be implemented in any number of ways, for example, by including preferably inert, solid objects (not shown), such as metal or plastic spheres, within the substances (e.g., 315A and 320A of FIG. 3) such that shaking of the cartridge results in the rupturing of the membranes (e.g., 305A) by the solid objects and the mixing of the contents of the container. The small solid objects are preferably sized and configured so as not to rupture the membranes inadvertently or obstruct the flow of substances.

In other embodiments the cartridge may take the form of a kit of pre-filled containers. For example, the kit may be sold as a box of four sealed, pre-filled containers, each containing a different coagulation affecting substance. These individual containers may then be individually inserted directly into reservoirs, or ports of a multiple coagulation test system, or first inserted into a holder to first couple the containers together into a cartridge, and used in the same manner as described above in reference to a cartridge. It should be noted that the structure, contents and number of containers in the kit may vary and the containers may take on any structure as described above in reference to containers of a cartridge.

The cartridges described herein may be manufactured out of any suitable material and in any in any suitable way. For example, a mold may be provided that has the shape of the cartridge where the filling of the mold with a liquid polymer and subsequent drying of the polymer forms the cartridge along with the membranes. After the molding, each section of the cartridge may be filled with the necessary coagulation promoting or coagulation inhibiting substance or substances as described herein. To facilitate the filling, each container, of the cartridge, may be molded with a vent, through which the filling is subsequently performed. After the filling, the vent may be closed, by melting, wax sealing, or any other method.

The cartridge may also be manufactured in sections. For example, each hollow section may be formed in a mold. Subsequently, a membrane may be adhered to one side of the section, and then the section may be filled with the necessary substance, and finally closed off with another membrane or attached in a series to a next section. These sections may then be coupled together to form containers, and containers may be coupled together to form a cartridge.

It should be noted that the cartridge 140, containers 140A-D, sections 405X-Z and 505, and reservoirs 95A-D may be made from any suitable material including, but not limited to, plastic, glass, polymer and other materials.

While the foregoing description and drawings represent the certain embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof and that various features of the embodiments described herein may be combined in different ways. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with each other or with other features. The presently disclosed embodiments are therefore to be considered in all respects as illustrative and not restrictive, the scope of the invention being indicated by the appended claims, and not limited to the foregoing description.

What is claimed is:

1. A system for determining an appropriate coagulation therapy for a patient, comprising:
   a multiple coagulation test system comprising a holder for containing the patient's blood, one or more coagulation detectors, multiple test wells, and multiple ports in fluid communication with the test wells;
   a disposable, single-use cartridge, which prior to use in evaluating the patient's blood, comprises:
   multiple containers, wherein each container includes:
      a potential coagulation therapy for administering to the patient, each potential coagulation therapy including one or more coagulants or anticoagulants in an amount suitable for use with evaluating blood clotting in a single patient to determine whether the potential coagulation therapy is appropriate for the patient; and
      a deformable seal at at least one end of the container;
   the cartridge configured to be coupled with the multiple coagulation test system, in which the cartridge has a first configuration prior to the cartridge being coupled with the multiple coagulation test system, in which the containers are sealed by the deformable seals, and a second configuration after the cartridge is coupled with the multiple coagulation test system, in which the containers are unsealed and in fluid communication with the ports of the multiple coagulation test system so the potential coagulation therapies in the containers may be released from the containers into the test wells of the multiple coagulation test system to allow for evaluation of clotting of the patient's blood with the potential coagulation therapies by the multiple coagulation test system; and
   wherein each of the potential coagulation therapies includes a different coagulant, anticoagulant or combination thereof as compared to another of the potential coagulation therapies; and
   wherein at least one of the containers includes multiple volumes that are separated from each other by one or more membranes and the potential coagulation therapy contained in the at least one container includes a different coagulant or anticoagulant of the potential therapy in each of the multiple volumes, and wherein each of the multiple volumes is in fluid communication with at least one port of the multiple coagulation test system when the cartridge is in the second configuration.

2. The system of claim 1 wherein at least one of the deformable seals is a removable seal.

3. The system of claim 1 wherein at least one of the deformable seals is a puncturable membrane.

4. The system of claim 1 wherein the one or more membranes are deformable membranes.

5. The system of claim 4 wherein the deformable membranes are puncturable membranes.

6. The system of claim 1 wherein the containers have an arrangement selected from the group consisting of: linear, circular; rectangular; polygonal; L-Shaped; two-dimensional; and multiple rows of containers.

7. The system of claim 1 wherein at least one container includes freeze-dried platelets having at least partial glycoprotein IIb/IIIa expression and secretory function.

8. The system of claim 1 further comprising at least one machine-readable identifier secured to the cartridge, the machine-readable identifier including information indicative of instructions for performing evaluations using the cartridge.

9. The system of claim 8 wherein the information indicative of instructions for performing evaluations using the cartridge includes information identifying the potential coagulation therapies included in the cartridge.

10. The system of claim 8 wherein the cartridge is adapted for use with the multiple coagulation test system and wherein the information indicative of instructions for performing evaluations using the cartridge includes information identifying instructions for control of the multiple coagulation test system.

11. The system of claim 8 wherein the machine-readable identifier is selected from the group consisting of: a radio frequency identification (RFID) tag, barcode, and pin code.

12. The system of claim 1 wherein at least one container includes freeze-dried platelets having at least partial glycoprotein IIb/IIIa expression.

13. The system of claim 1 wherein at least one container includes freeze-dried platelets having at least partial secretory function.

14. The system of claim 1 wherein the multiple coagulation test system further includes one or more puncture elements configured to pierce the deformable seals of the containers when the cartridge is in the second configuration.

* * * * *